United States Patent [19]

Brennan et al.

[11] Patent Number: 4,477,470

[45] Date of Patent: Oct. 16, 1984

[54] METHOD FOR PRODUCING DIURESIS USING M-AMINO-α-METHYLPHENETHYLAMINE

[75] Inventors: Francis T. Brennan, Springfield, Pa.; Genevieve F. Sosnowski, Wilmington, Del.; Joseph Weinstock, Phoenixville, Pa.

[73] Assignee: SmithKline Beckman Corporation, Philadelphia, Pa.

[21] Appl. No.: 543,737

[22] Filed: Oct. 20, 1983

[51] Int. Cl.$^3$ .......................................... A61K 31/135
[52] U.S. Cl. ..................................................... 424/330
[58] Field of Search ......................................... 424/330

[56] References Cited

U.S. PATENT DOCUMENTS 4,015,011  3/1977  Schromm et al. .................. 424/324

FOREIGN PATENT DOCUMENTS 1352392  5/1974  United Kingdom ............... 424/330

Primary Examiner—Albert T. Meyers
Assistant Examiner—Joyce L. Morrison
Attorney, Agent, or Firm—William H. Edgerton; Richard D. Foggio; Alan D. Lourie

[57] ABSTRACT m-Amino-α-methylphenethylamine, when administered internally, induces water diuresis in patients having edema.

6 Claims, No Drawings

METHOD FOR PRODUCING DIURESIS USING M-AMINO-α-METHYLPHENETHYLAMINE

This invention comprises pharmaceutical compositions and methods for producing water diuresis in a subject in need thereof. The active ingredient used in this invention is m-amino-α-methylphenethylamine, one of its optical isomers or a salt of either the racemate base or an optical isomer base.

BACKGROUND OF THE INVENTION

U.S. Pat. No. 4,015,011 discloses the use of m-amino-α-methylphenethylamine as an intermediate for preparing various N-acyl end products which are alleged to be hypertensives due to their sympathomimetic activity. The compound is included in the generic group described in the specification of the '011 patent but it is not claimed and no specific biological activity is described for this species. Example 1 of this patent describes the chemical preparation of m-amino-α-methylphenethylamine, its maleate and hydrochloride salts.

m-Amino-α-methylphenethylamine is a member of the amphetamine family of compounds which has long been the subject of investigation in the pharmaceutical art as sympathomimetic agents, for example, see Great Britain Pat. No. 1,352,392. The aquaretic activity, which has been found by the present applicants, is unexpected both within the amphetamine series of compounds, as demonstrated by the data in the comparative example outlined hereinafter, and within the diuretic field.

DESCRIPTION OF THE INVENTION

This invention comprises the method of producing water diuresis in a subject in need thereof by administering internally, orally or parenterally, to the animal or human patient an effective but nontoxic quantity of m-amino-α-methylphenethylamine. Representative dosage unit ranges from which an effective dose may be chosen, for a 75 kg subject, are from 75–750 mg of base to be administered orally from 1–4 times daily or from 5–150 mg of base to be administered parenterally from 1–4 times daily. Overt sympathomimetic side effects such as pressor or central nervous system activity were seldom observed with oral dosing at effective aquaretic dosages but were observed with intravenous dosage units selected from the upper dose range given above.

A preferred single dose is selected from the range of 1–15 mg/kg of base equivalent to be orally administered several times a day. Especially, 5 mg/kg is used.

The subject in need of water diuresis is one whose edematous condition is due to hypertension, hepatic cirrhosis, congestive heart failure or a traumatic injury or disease.

In addition to the water diuretic activity described herein, m-amino-α-methylphenethylamine has also been found to be strongly natriuretic in hydropenic monkeys with a urine output 50% over that of the control animals. The active ingredient at 10 mg/kg and 30 mg/kg orally in Brattleboro rats (devoid of vasopressin) demonstrated diuretic activity compared with controls.

The active ingredient is conveniently used in the form of a nontoxic, diuretically active salt which is prepared by reacting the base with a pharmaceutically acceptable acid such as hydrochloric, sulfuric, hydrobromic, methane sulfonic acid, ethane disulfonic acid, phosphoric, sulfamic, acetic, succinic, maleic or acid.

The salt forms are prepared by reacting the base of the active ingredient with an excess of the selected acid in a suitable solvent system. m-Amino-α-methylphenethylamine is dibasic and, thereby, reacts with two mole-equivalents of acid.

The active ingredient of this invention is a racemic mixture of optical isomers. The dextro-rotatory and levo-rotatory isomers of m-amino-α-methylphenethylamine were prepared by assymetric synthesis. The dextro isomer base (m.p. 93.5°–99.5° C., $\alpha_D^{25}$ (1%, H$_2$O) = +39.9°) is more active than is the levo isomer base hydrate (m.p. 79°–80° C., $\alpha_D^{25}$ (1%, H$_2$O) = −30.2°), however, both isomers have substantial diuretic activity.

The active ingredients of this invention in the dosage unit quantities described above are combined with a pharmaceutical carrier and manufactured into forms for internal administration.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use, syrups, peanut oil, olive oil or water for soft gelatin capsules. Similarly the carrier or diluent may include any time delay material well known to the art, such as cellulose derivatives or glyceryl esters.

A wide variety of pharmaceutical forms can be employed. Thus, if a solid carrier for oral administration is used, the preparation can be tableted or placed in hard gelatin capsule, powder, regular or sustained release pellet, troche or lozenge form. The amount of solid carrier will vary widely but, preferably, will be from about 25 mg to about 1 g. If a liquid carrier is used, the preparation will be in the form of a syrup, emulsion, soft gelatin capsule, sterile injectable liquid such as an ampul, or aqueous or nonaqueous liquid suspension. Several unit doses may be combined such as in a multi-dose vial or intravenous drip preparation.

The novel pharmacodynamic activity which is available by using variations of this invention has been demonstrated by standard procedures in the rat, dog and monkey. The following data and procedures are selected to illustrate the invention.

EXAMPLE 1

Protocol for the anti-ADH rat procedure:

Groups of 8 adult rats are fasted from food and water for approximately 16 hours prior to testing. The test procedure is as follows: Animals are housed 4 per metabolism cage. An oral water load (2.5 ml/100 g) is given 2 hours prior to the start of the test. Drug is administered orally or parenterally to the test group at the 0-hour. At the same time, both control and test groups receive 1 mμ Pitressin/100 g body weight, s.c., and a gavage of 0.21% sodium chloride solution at a dose of 5 ml/100 g body weight. One hour later urine volume is recorded. The same animals receive a repeated dose of Pitressin, s.c. and a second gavage of 0.21% sodium chloride solution at a dose of 5 ml/100 body weight. Urine samples from both control and test groups are collected at the end of 2 hours. Test values are recorded at % of the volume of the saline load excreted (cumulative volume, 1–2 hours), mEq/rat electrolyte excreted, mg/rat urea excreted and osmolality in milliosmoles/L.

Based on control data (n=50), a compound is considered to have significant activity ($p \leq 0.05$) if, at the end of 2 hours, it produces a volume of the saline load excreted ≧18.5%; sodium excretion ≧0.6074 mEq/rat; potassium excretion ≧0.1885 mEq/rat; and urine osmolality ≦414 milliosmoles/L.

Results:

| Dose, mg/kg salt | base | No. of Animals | % H₂O - Load Excreted 2 hrs. | Na Excretion mEq/Group | K Excretion mEq/Group | Osmolality Milliosmoles/L |
|---|---|---|---|---|---|---|
| Pitressin 1 mU/100 g (s.c.) | | | | | | |
| | | 8 | 13.1 | 2.77 | 0.76 | 585 |
| m-Amino-α-methylphenethylamine sulfate (oral) | | | | | | |
| 1 | .6 | 8 | *30.3 | *7.28 | *1.55 | 577 |
| 5 | 3 | 8 | *38.0 | *8.86 | *1.21 | 505 |
| 10 | 6 | 8 | *46.7 | *10.53 | *1.39 | 502 |
| 20 | 12 | 8 | *60.0 | *10.41 | *1.51 | 406* |
| 30 | 18 | 8 | *58.5 | *11.62 | *1.40 | 421** |
| 60 | 36 | 8 | *56.5 | *10.30 | *1.39 | 392*,** |

*significant
**salivation polyhidrosis depression

EXAMPLE 2

Protocol for the saline-loaded rat procedure:

Adult male albino rats of the Wistar strain, weighing 200 to 400 g each, are fasted overnight with water allowed ad lib. The following morning the rats are divided into groups of 4 in such a way that their weights are evenly distributed throughout the series. Eight rats (2 groups of 4 each) are used as controls for each group of animals and for each dose of test compounds. Each control rat receives an oral load of 2.5 ml or 0.9% sodium chloride/100 g of body weight administered by means of a graduated syringe fitted with a small rubber catheter. The desired mg/kg dose of test compound is added to each 25 ml of saline contained in a vessel whose contents are continuously stirred with a magnetic stirrer so that insoluble compounds are uniformly distributed. The saline-drug solution (or suspension) is administered orally to each rat of a test group at a volume of 2.5 ml/100 g of body weight. Immediately after drug administration, the rats are placed in metabolism cages with each subgroup of 4 rats in a separate cage. Urine is collected for the next 5 hours. The total 5-hour urine volume for each group of 8 rats is then measured.

The results are expressed in terms of the percent of the volume of the saline load excreted during the 5-hour period. Volume of urine (8 rats)/Volume of saline load (8 rats)×100. Control groups excrete an average of 60% of the volume of the saline load with a standard deviation of 10.8%. The excretion of 82% of the volume of the saline load administered is considered a positive diuretic effect within 95% confidence limits.

Results:

| Dose mg/kg p.o. | Percent Excreted | Effect % Excreted (Test − Control) |
|---|---|---|
| Control | 60 | — |
| m-Amino-α-methylphenethylamine sulfate | | |
| 15 (9.15 mg/kg base) | 147 | 87 |
| 30 (18.3 mg/kg base) | 159 | 99 |

EXAMPLE 3

In related procedures, m-amino-α-methylphenethylamine sulfate, demonstrated aquaretic activity in the hydropenic rat at 10 mg/kg, p.o. and was saluretic in the sodium deficient rat at 15 and 30 mg/kg, p.o.

EXAMPLE 4

Dog Renal Clearance Protocol—Phosphate Mannitol Infusion:

A modification of the method of Wiebelhaus et al., (Archives internationales de Pharmacodynamie et de Therapie. Vol. 169, No. 2, 429–451, 1967), is used for renal clearance studies in adult, trained, unanesthetized, fasted, female mongrel dogs, lightly restrained on their backs on a cradle-like board constructed specifically for this purpose. The effect of compound upon kidney function is determined by measurement of effective renal plasma flow (RPF), glomerular filtration rate (GFR), and filtration fraction (FF). Urine volume, pH and electrolyte excretion are also determined. The clearance of free water is calculated from serum and urinary osmolalities.

All dogs are given an oral water load of 500 ml tap water thirty minutes prior to initiation of the study. Using a constant infusion pump, the dogs are infused intravenously at 3 ml/minute throughout the course of the experiment with a 4% mannitol-phosphate buffer solution, pH 7.4. Glomerular filtration rate is determined by clearance of creatinine and effective renal plasma flow by the clearance of p-aminohippurate (PAH). These clearances are determined simultaneously by including 0.4% creatinine and 0.08% PAH in the infusion solution. Suitable plasma levels of creatinine and PAH are obtained by a thirty minute infusion of this solution to obtain equilibrium prior to starting of the initial urine collection ($U_1$). In addition, 1.5 ml/kg of a 1% creatinine solution in phosphate buffer is injected intravenously fifteen minutes prior to collection of $U_0$. Replicate urine collections are obtained at ten minute intervals throughout the experiment. The bladder is emptied by an indwelling catheter and complete urine collections are assured by rinsing the bladder with 10 mls of warm water at the end of each collection interval. This procedure is followed by an air washout. Venous blood samples are drawn from an indwelling catheter at the mid-point of each clearance period.

Serum and urine osmolalities are determined by freezing point depression on freshly obtained samples. Urine volume and pH are recorded at the time of collection. Serum and urine samples are stored frozen, after collection, until analyzed. Analyses for sodium and potassium are made using the AutoAnalyzer flame photometer and for chloride, creatinine and PAH, by colorimetry, using standard AutoAnalyzer methodology. These analyzes are made simultaneously on each sample. Peak intensities are identified electronically, recorded by "on-line" teletype, stored and subsequently analyzed mathematically by time-shared computer against appropriate standards. Data are computed from linear least square regression lines, and quality control standards are analyzed simultaneously to evaluate system reproducibility and reliability.

The bladder is emptied ($U_0$) upon beginning the study and three control clearances ($U_1$–$U_3$ Phase I) are obtained. Compound is given either orally in a water suspension by stomach tube or by intravenous (stat) injection or infusion.

Results:

| FOUR DOGS GIVEN m-AMINO-α-METHYL-PHENETHYLAMINE SULFATE AT 10 MG/KG P.O. | | | | |
|---|---|---|---|---|
| Parameter | Control Phase I Clearances 1–3 | Phase II Clearances 4–6 | Post Drug Phase III Clearances 7–9 | Phase IV Clearances 10–12 |
| | Mean | % Change of Post-Drug Phase Mean from Phase I Mean | | |
| RPF (ml/min) | 173.91 | −1.38 | 4.09 | 0.97 |
| GFR (ml/min) | 61.17 | 10.50* | 27.79* | 19.94* |
| | Mean | Difference Between Post-Drug Phase and Phase I | | |
| Na+ % Excreted | 0.87 | −0.54 | −0.36 | −0.06 |
| K+ % Excreted | 17.26 | −2.43 | −4.22 | −3.10 |
| Cl− % Excreted | 0.30 | −0.16 | 0.03 | 0.27 |
| FF (GFR/RPF) | 0.35 | 0.03 | 0.08* | 0.06* |

*Statistically significant at P less than or equal to 0.05

| TWO DOGS GIVEN m-AMINO-α-METHYL-PHENETHYLAMINE SULFATE AT 10 MG/KG P.O. | | | | |
|---|---|---|---|---|
| Parameter | Control Phase I Clearances 1–3 | Phase II Clearances 4–6 | Post Drug Phase III Clearances 7–9 | Phase IV Clearances 10–12 |
| | Mean | % Change of Post-Drug Phase Mean from Phase I Mean | | |
| RPF (ml/min) | 133.98 | 7.80 | 5.44 | −17.34 |
| GFR (ml/min) | 66.31 | 14.0 | 29.14* | 25.96* |
| | Mean | Difference Between Post-Drug Phase and Phase I | | |
| Na+ % Excreted | 0.04 | 0.02 | 0.04 | 0.04 |
| K+ % Excreted | 4.50 | −0.32 | −0.23 | 0.13 |
| FF (GFR/RPF) | 0.49 | 0.01 | 0.11* | 0.21* |

*Statistically significant at P less than or equal to 0.05

In Examples 4 and 5, a surprising increase in the glomerular filtration rate (GFR) was demonstrated. This effect, without an appreciable change in renal plasma flow or electrolyte excretion, is virtually unique with this compound.

EXAMPLE 6

In the water-loaded or hydropenic, anti-ADH protocol in dogs, 2.0 mg/kg, i.v.; 2.5 mg/kg, i.v.; 10 mg/kg, i.v. or 10 mg/kg p.o., of m-amino-α-methylphenethylamine sulfate gave substantial increase in urine volume and decreases in urinary osmolality in several different runs.

EXAMPLE 7

In the anti-ADH rat protocol described above, d-or S(+)-m-amino-α-methylphenethylamine, as the base given orally, gave the following results.

| Dose, mg/kg | No. of Animals | Urine Volume - % Saline Excreted (Cumulative) 2 hrs | Na Excretion mEq/rat | K Excretion mEq/rat | Urine Osmolality Milliosmoles/L. |
|---|---|---|---|---|---|
| 0 | 8 | 42.6 | .0841 | .0446 | 92 |
| Pit 1 mμ/100 g | 8 | 3.3 | .0601 | .0315 | 822 |
| 10 | 8 | *40.3 | *.8027 | .1306 | *315 |
| 30 | 8 | *59.1 | *.9725 | .1630 | *248 |

1-or R(−)-m-Amino-α-methylphenethylamine, as the base given orally, gave the following results:

| Dose, mg/kg | No. of Animals | Urine Volume - % Saline Excreted (Cumulative) 2 hrs | Na Excretion mEq/rat | K Excretion mEq/rat | Urine Osmolality Milliosmoles/L. |
|---|---|---|---|---|---|
| 0 | 8 | 50.6 | .0736 | .0499 | 87 |
| Pit 1 mμ/100 g | 8 | 1.6 | .0470 | .0253 | 1233 |
| 10 | 8 | *21.5 | *.5451 | .0960 | 418 |
| 30** | 8 | *38.5 | *.8781 | .1326 | *355 |

**Side Effects: Piloerection

EXAMPLE 8 m-Amino-α-methylphenethylamine sulfate (75 mg of base) is mixed with 200 mg of lactose and 1 mg of magnesium stearate. The mixture is filled into a hard gelatin capsule which is administered orally to a subject in need of diuretic treatment.

EXAMPLE 5

Dog Renal Clearance Protocol—Glucose Infusion:

COMPARATIVE EXAMPLE

The following data demonstrate, in the anti-ADH rat protocol outlined above, the water diuretic effect of m-amino-α-methylphenethylamine to be unique compared with its position isomers and with other m-substituted amphetamines:

| Compound (base) | Dose mg/kg, p.o. | Cumulative Volume % Excreted | | VOSM |
|---|---|---|---|---|
| | | 1 hr. | 2 hr. | |
| m-amino-α-methyl-phenethylamine | 10 | 105.7 | 79.6 | 221 |
| | 30 | 84.4 | 78.1 | 220 |
| p-amino-α-methylphenethyl-amine | 10 | 35.0 | 21.2 | 384 |
| | 30 | 56.7 | 39.6 | 336 |
| o-amino-α-methylphenethyl-amine | 10 | 47.1 | 27.2 | 381 |
| | 30 | 71.9 | 46.7 | 301 |
| m-hydroxy-α-methyl-phenethylamine | 10 | 11.7 | 11.1 | 572 |
| | 30 | 14.9 | 13.0 | 466 |
| m-methoxy-α-methyl-phenethylamine | 10 | 16.4 | 9.9 | 539 |
| | 30 | 7.6 | 15.3 | 340 |

What is claimed is:

1. A method of producing water diuresis or saluresis in a human or animal patient in need thereof comprising administering orally or parenterally to said patient a nontoxic, diuretic quantity of m-amino-α-methylphenethylamine, an optical isomer thereof or a pharmaceutically acceptable, acid addition salt thereof.

2. The method of claim 1 in which the administration is orally to a patient in need of water diuresis.

3. The method of claim 1 in which the compound is m-amino-α-methylphenethylamine.

4. The method of claim 1 in which the compound is m-amino-α-methylphenethylamine as the sulfate salt.

5. The method of claim 1 in which the quantity of compound is selected from 75–750 mg of said compound administered orally.

6. The method of claim 1 in which the quantity of compound is selected from 5–150 mg of said compound administered parenterally.

* * * * *